United States Patent
Jun

(10) Patent No.: US 11,918,663 B2
(45) Date of Patent: Mar. 5, 2024

(54) METHOD FOR GENERATION OF OPALESCENCE IN DENTAL RESTORATIONS

(71) Applicant: Jensen Industries Inc., North Haven, CT (US)

(72) Inventor: Yoonho Jun, Weatogue, CT (US)

(73) Assignee: JENSEN INDUSTRIES INC., North Haven, CT (US)

(*) Notice: Subject to any disclaimer, the term of this patent is extended or adjusted under 35 U.S.C. 154(b) by 219 days.

(21) Appl. No.: 16/793,783

(22) Filed: Feb. 18, 2020

(65) Prior Publication Data

US 2020/0261323 A1 Aug. 20, 2020

Related U.S. Application Data

(60) Provisional application No. 62/806,192, filed on Feb. 15, 2019.

(51) Int. Cl.
| | |
|---|---|
| *A61K 6/818* | (2020.01) |
| *A61K 6/816* | (2020.01) |
| *A61K 6/836* | (2020.01) |
| *A61K 6/871* | (2020.01) |
| *A61K 6/884* | (2020.01) |

(52) U.S. Cl.
CPC .............. *A61K 6/818* (2020.01); *A61K 6/816* (2020.01); *A61K 6/836* (2020.01); *A61K 6/871* (2020.01); *A61K 6/884* (2020.01)

(58) Field of Classification Search
CPC ..................................................... A61K 6/802
See application file for complete search history.

(56) References Cited

U.S. PATENT DOCUMENTS 5,432,130 A 7/1995 Rheinberger et al.
2004/0245663 A1* 12/2004 MacDougald .... C04B 35/62218
264/16

(Continued)

FOREIGN PATENT DOCUMENTS

DE 10351885 A1 5/2014
EP 2583660 A1 4/2013

(Continued)

OTHER PUBLICATIONS

International Search Report dated May 28, 2020 in corresponding International Patent Application No. PCT/US2020/018648.

(Continued)

*Primary Examiner* — Michael F Pepitone
(74) *Attorney, Agent, or Firm* — Troutman Pepper Hamilton Sanders LLP

(57) ABSTRACT

Disclosed herein are methods for creating opalescence in dental materials and restorations, compositions used in such methods, and the resultant dental materials and restorations. More particularly, the opalescence may be created by directly embedding opalescent particles into a matrix material. In some embodiments, photonic crystals are embedded in the dental material to achieve the opalescent effect. Photonic crystal particles may be embedded in dental materials matrices such as ceramics, composites, and polymers, and can generate opalescence in the materials. Some embodiments disclose compositions for applying the opalescence to a dental restoration.

11 Claims, 1 Drawing Sheet

Light reflection by photonic crystals (opalescence agents) dispersed in a matrix

(56) References Cited

U.S. PATENT DOCUMENTS

| | | | |
|---|---|---|---|
| 2005/0064369 A1* | 3/2005 | Zel | A61K 6/16 433/203.1 |
| 2012/0120984 A1 | 5/2012 | Vanier et al. | |
| 2018/0098918 A1 | 4/2018 | Banasiak et al. | |
| 2019/0077936 A1* | 3/2019 | Liao | B01J 20/28042 |

FOREIGN PATENT DOCUMENTS

| | | | |
|---|---|---|---|
| FR | 2926460 A1 | 7/2009 | |
| FR | 2933610 A1 | 1/2010 | |
| WO | 2010045105 A1 | 4/2010 | |
| WO | 2010094994 A1 | 8/2010 | |
| WO | 2018031821 A1 | 2/2018 | |
| WO | WO-2018031821 A1 * | 2/2018 | A61K 6/16 |

OTHER PUBLICATIONS

Partial Search Report dated Nov. 16, 2022 in Corresponding EP Application 20755428.8.
Chabanov et al. (2004). Avoiding cracks in self-assembled photonic band-gap crystals. Applied Physics Letters, 84 (18), 3573-3575. https://doi.org/10.1063/1.1737066.

* cited by examiner

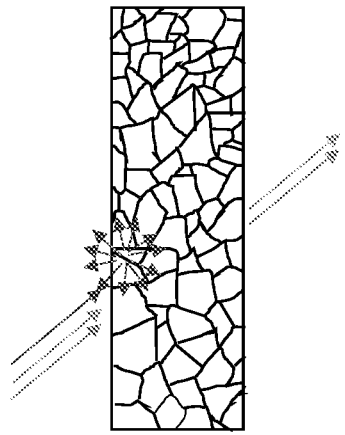
FIG. 1a Scattering by nanoparticles dispersed in a matrix
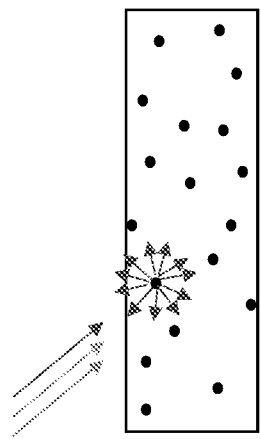
FIG. 1b Scattering at grain boundaries
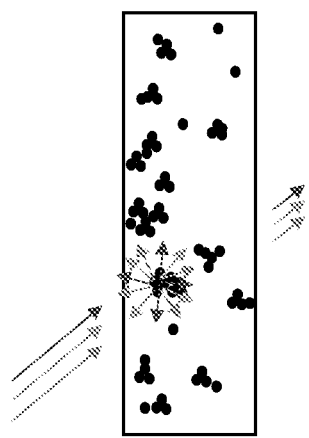
FIG. 1c Scattering by aggregates (white opaque)
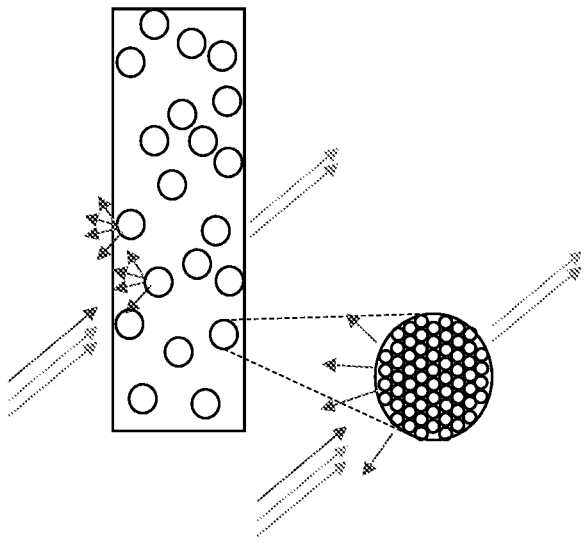
FIG. 1d Light reflection by photonic crystals (opalescence agents) dispersed in a matrix

METHOD FOR GENERATION OF OPALESCENCE IN DENTAL RESTORATIONS

CROSS REFERENCE TO RELATED APPLICATIONS

This application claims the benefit of priority of U.S. Patent Application Ser. No. 62/806,192, filed on Feb. 15, 2019, entitled "Method for Generation of Opalescence in Dental Restorations," the entire contents of which are hereby incorporated by reference herein.

FIELD

This disclosure relates to methods for creating opalescence in dental materials and restorations, and such dental materials and restorations. More particularly, the opalescence may be created by directly embedding opalescent particles into a matrix material. In some embodiments, photonic crystals are embedded in the dental material to achieve the opalescent effect. Photonic crystal particles may be embedded in dental materials matrices such as ceramics, composites, and polymers, and can generate opalescence in the materials.

BACKGROUND

Opalescence is a term that describes an optical characteristic of opal stones. The term refers to a color change seen when opals are viewed in different lighting situations; opals appear to be one color in reflected light, and a complementary color in transmitted light. That is, light reflected off the surface of an opal is one color and light passing through the opal is a complementary color.

Natural teeth have opalescence due to light scattering caused by hydroxyapatite nanocrystals. When incident light penetrates into the teeth, blue light is preferentially scattered back to the side where light is coming from, which gives the teeth a bluish-white appearance. However, in thin areas, light can pass through the teeth, and because they are opalescent, those areas where light is transmitted appear red to orange in color. Though opalescence in natural teeth is from both enamel and dentin, enamel is the main source of the opalescence.

Similarly, the opal effect can be created in a dental material by carefully controlling how light is scattered by that material. There are several known ways of achieving the effect, most of which require nano-scale particles for light scattering.

One method of making opalescent substances is by the nucleation and growth of nano-sized crystals in a matrix phase. By controlling the size of the crystals, the wavelength (and thus the color) of scattered light can be modulated. However, to achieve opalescence in this manner requires very precise control over the temperature and holding time of the nucleation and growth cycles as well as subsequent thermal cycling, or else the opalescent effect is lost. Therefore, this method is not suitable for every situation where an opalescent material might be desired.

Another method involves mixing nanoparticles with a matrix material. This method has its own challenges; the nanoparticles must be well dispersed in the matrix, and nanoparticles agglomerate readily during mixing or heat treatment. Agglomerated particles cause random scattering of light and result in the material being white and opaque rather than the desired opalescence.

A different approach for making opalescent substances, specifically ceramic materials, uses nanoparticles as a starting material. With this technique, nano-sized powder is compacted and sintered like conventional ceramic powder. If the optical characteristics of the ceramic are suitable, and the final grain size can be maintained below 400 nm, an opalescent ceramic can be produced. However, keeping the grain size small and uniform is very challenging by using conventional sintering processes. Usually, it requires unconventional sintering techniques such as a hot isostatic press and plasma assisted sintering which is performed at lower temperature for shorter holding time than conventional sintering.

Applicant has invented a new, efficient, and effective way of achieving opalescence in dental materials and dental materials and restorations having such opalescent qualities. This new method offers distinct advantages to the prior art. The above described methods all require much more careful control of manufacturing parameters such as time, temperature, and particle size distribution than the method disclosed herein.

Furthermore, the above described methods all achieve opalescence through highly controlled scattering of light by either second phase particles or grain boundaries, which increase the opacity of the material. As a result, it is not possible to achieve an opalescent effect in a very thin section of a translucent material using these methods. The present invention is particularly well suited to creating translucent materials that exhibit opalescence in very thin (0.1 to 0.5 mm) thicknesses, such as those used for esthetic dental restorations.

SUMMARY

In this disclosure, opalescence has been achieved by incorporating photonic crystal particles in dental materials. Previously, opalescence has been imparted to dental materials by controlling scattering through careful distribution of a second phase or by precise control of microstructure. Embodiments described herein do not rely on either of those ideas, but instead utilizes photonic crystal particles which reflect light with specific color instead of scattering light in broad range of wavelength. The intensity of reflected light by photonic crystals is much stronger than what can be achieved by scattering. Therefore, strong opalescence can be achieved even in a very thin film, for example, a layer of glaze ceramic applied to a dental restoration.

Some embodiments provide a dental material comprising one or more dental matrices; and one or more photonic crystal.

In some embodiments, the one or more dental matrices comprises a dental glaze, a dental porcelain, a dental ceramic, a dental composite, a dental resin, a dental polymer, or a combination thereof.

In some embodiments, the dental ceramic contains at least one of alumina, zirconia, glass ceramic, leucite reinforced glass, glass infiltrated ceramic, or a mixture or solid solution of two or more of them.

In some embodiments, the photonic crystal is a synthetic opal.

In some embodiments, the photonic crystal is a synthetic opal partially or fully infiltrated with ceramic, organic, organic-inorganic hybrid material, or mixture of two or more of them.

In some embodiments, the infiltrating ceramic material contains one or more of alumina, zirconia, titania, silica, yttria, zinc oxide, hafnia, tin oxide, indium oxide, ceria, niobium oxide, tantalum oxide, germanium oxide, gallium oxide, and scandium oxide.

In some embodiments, the infiltrating ceramic material contains one or more materials that can be converted to alumina, zirconia, titania, silica, yttria, zinc oxide, hafnia, tin oxide, indium oxide, ceria, niobium oxide, tantalum oxide, germanium oxide, gallium oxide, scandium oxide or mixture or solid solution of two or more of them when it goes through chemical, thermal, light, pressure treatment or combination of two or more treatments.

In some embodiments, the organic-inorganic hybrid material contains one or more materials that can be converted to alumina, zirconia, titania, silica, yttria, zinc oxide, hafnia, tin oxide, indium oxide, ceria, niobium oxide, tantalum oxide, germanium oxide, gallium oxide, scandium oxide, or mixture or solid solution of two or more of them when it goes through chemical, thermal, light, pressure treatment or combination of two or more treatments.

In some embodiments, the organic material of the organic-inorganic hybrid material consists of one or more of monomer or polymer or mixture of a least one monomer and one polymer.

In some embodiments, the photonic crystal is an inverse opal.

In some embodiments, the inverse opal is made of ceramic, organic, organic-inorganic hybrid material, or mixture of two or more of them.

Some embodiments provide a method of making a dental material comprising combining one or more photonic crystals with one or more dental matrices.

In some embodiments, the one or more dental matrices is a dental glaze, dental porcelain, dental ceramic, dental composite, dental resin, dental polymer, or a combination thereof.

In some embodiments, the dental ceramic contains at least one of alumina, zirconia, glass ceramic, leucite reinforced glass, glass infiltrated ceramic, and mixture or solid solution of two or more of them.

Some embodiments provide a composition for imparting opalescence to a dental restoration, the composition comprising a ceramic component, an opal component, and a liquid component.

In some embodiments, the composition comprises about 50-85% by weight of a ceramic component; about 1-20% by weight of opal component; and the balance being a liquid component.

In some embodiments, the ceramic component is a ceramic base present at about 50-85% by weight.

In some embodiments, the opal component is present at about 2-6% by weight.

In some embodiments, the opal component is present at about 6-12% by weight.

In some embodiments, the ceramic component is a glaze base present at about 50-65% by weight.

In some embodiments, the opal component is present at about 6-15% by weight.

Some embodiments, comprise less than about 2% by weight of a viscosity modifier.

Some embodiments comprise less than about 1% by weight of a fluorescing agent.

Some embodiments comprise less than about 2% by weight of a viscosity modifier; and less than about 1% by weight of a fluorescing agent.

BRIEF DESCRIPTION OF THE DRAWINGS

FIGS. 1a through 1d depict light scattering effects by various materials. FIG. 1d (lower right corner) depicts the effects achieved by the methods and materials herein.

DETAILED DESCRIPTION

According to the methods described herein, opalescence maybe be created by directly embedding opalescent particles into a matrix material. In particular, photonic crystals can be embedded in the dental material to achieve the opalescent effect. This disclosure is about using photonic crystals as an opalescent agent for dental materials. Photonic crystal particles may be embedded in dental materials matrix such as ceramics, composites, and polymers can generate opalescence in the materials.

A crystal is a material in which atoms or molecules are arranged periodically. A photonic crystal is an ordered structure in which the refractive index varies periodically on a length scale comparable to the wavelength of light of interest. Light experiences a periodic potential when it propagates through a photonic crystal just as electrons are affected by a periodic potential in a conventional crystal. In photonic crystals the periodic potential is due to a lattice of dielectric materials instead of atoms or molecules. Light in a photonic crystal is forbidden to propagate within certain energies in certain directions. In other words, light is reflected in certain directions. When incident light is white light, light with a certain wavelength range is reflected. The angle and wavelength range are controlled by the effective refractive index and periodicity. Depending on the number of dimensions in which photonic crystals have periodicity, there are one dimensional, two dimensional, and three dimensional photonic crystals.

Photonic crystals formed from colloid particles are called colloidal crystals or synthetic opals. Synthetic opals can be made by packing colloidal particles into regularly ordered structures. Packing can be done by sedimentation, controlled drying, selective deposition on pre-patterned sites, injection of droplets of colloid suspension into air or another immiscible liquid and subsequent drying, or centrifugation of colloidal suspensions. Centrifugation is the fastest method to make photonic crystals in large quantity. Silica spheres and polymer spheres are most frequently used for synthetic opals.

In addition to synthetic opals, there are other kinds of photonic crystals that can be used to create an opalescent effect. For example, a synthetic opal can be used as a framework to create what is known as an "inverse opal". Inverse opals are created by infiltrating synthetic opals with a different material, (e.g., titania, silica, zirconia or polymer), then removing the silica or polymer lattice by chemical dissolution or thermal decomposition.

A third type of photonic crystal can be created by partially or fully infiltrating the lattice of a synthetic opal with a different material, e.g., titania, silica, zirconia or polymer, but not inverting the structure by removing the synthetic opal.

The characteristic reflective color of photonic crystals is dependent upon the effective refractive index of the crystal and on the periodicity of the lattice. By infiltrating synthetic opals or inverting the opals, one can therefore modify the characteristic reflective color of the crystal by changing the effective refractive index. Similarly, the periodicity of the crystals can be controlled by altering the diameter of the spheres used to create the crystals. Equation (1) is a formula for reflection peak in synthetic opals, partially or fully infiltrated opals, or inverse opals with face centered cubic lattice.

$$\lambda = 2dn_{eff} = \left(\frac{\pi}{3\sqrt{2}\,\phi}\right)^{1/3}\left(\frac{8}{3}\right)^{1/2} D(n_p^2\phi + n_m^2[1-\phi])^{1/2} \quad (1)$$

where d is lattice spacing, $n_{eff}$ is the effective refractive index, D is particle diameter, φ is particle volume fraction, $n_p$ and $n_m$ are refractive indices of the particle and the media filling voids. This formula provides guidance as to how one can achieve a desired reflective wavelength by choice of materials and sphere size.

As described herein, synthetic opals and infiltrated synthetic opals were used for demonstrating use of photonic crystals as opalescence agents in dental applications such as ceramics, composites, and polymers. Synthetic opals were formed by centrifugation of silica sphere suspension.

General Procedure for Making Synthetic Opals.

Silica spheres with either about 180 nm size or 220 nm size (other sizes may be used) and ethanol were added to each centrifuge tube to make 20 wt. % ethanolic suspension of silica spheres. The size of the silica sphere affects the periodicity which affects the wavelength of reflected light, thus, silica spheres may be chosen of any size based on the desired light. For example, silica spheres may range in size from about 140 nm to about 370 nm. The size and the reflective index of the silica sphere determines the reflected wavelength (i.e., the reflected color). The suspension was sonicated to break aggregates of the silica spheres. Centrifugation at low speed was done to remove large aggregates from the suspension. The supernatant suspension was decanted and transferred to another centrifuge tube. Sonication was applied again and centrifugation at high speed was done to form synthetic opals. Ethanol was decanted and the synthetic opal was dried at room temperature. The dried synthetic opal was heated at 600° C. for 4 h for consolidation of the opal. The synthetic opal was then subject to further treatment to prepare opalescent dental materials.

In its most general sense, the methods herein incorporate synthetic opals, i.e., photonic crystals, into dental materials via mixing and other techniques.

Several of the methods include the use of a glazing powder. The glazing powder is an unpigmented, clear glazing porcelain of an appropriate firing temperature Any glazing powder suitable for use in dental restorations may be employed. In some instances, the synthetic opals could be incorporated into a glaze paste product.

In some embodiments, the photonic crystals can be mixed with a glazing powder. To which an organic liquid may later be added to obtain a paste.

In other embodiments, the photonic crystals may be added to an existing paste glaze product.

Glazing powder or paste glaze products including but not limited to layering materials, glazing materials, structure building materials, are any that are suitable for use in dental restorations.

In some embodiments, the photonic crystal powder may be incorporated into any dental ceramic, polymer, resin, composite, or other dental material.

Examples 1 and 5, below, describe a method of creating a glaze capable of imparting an opalescence characteristic when applied to a zirconia restoration and fired. The heat-treated opals obtained from the general procedure are ground into powder. Opal powder smaller than 63 μm was further milled in the ethanolic suspension into smaller particles. The particles were dried. opal powder and glaze powder were mixed at a ratio of about 1:9 parts by weight. A range of about 1:1 to about 1:199 by weight may be employed. In some embodiments, the range is about 1:2 to about 1:99. In some embodiments, the range is about 1:3 to about 1:49. The mixed powder was made into a paste and applied to a zirconia restoration. The glaze layer with opal particles was fired according to the firing schedule of the glaze.

In examples 2 and 6, the heat-treated opal chunks (i.e., aggregated) are infiltrated with titania by the following procedure. The chunks were immersed in titanium isopropoxide for 2-10 hours and dried. In some embodiments, the chunks were allowed to sit in the isopropoxide for about 4 hours. The dried chunks were heated at 600° C. for 1 hour to yield titania infiltrated opal chunks. The titania infiltrated opal chunks were ground into powder. Titania infiltrated opal powder smaller than 63 μm was further milled in the ethanolic suspension into smaller particles. The particles were dried. Opal powder with titania infiltration and glaze powder were mixed at a ratio of about 1:9 parts by weight. A range of about 1:1 to about 1:199 by weight may be employed. In some embodiments, the range is about 1:2 to about 1:99. In some embodiments, the range is about 1:3 to about 1:49. The mixed powder was made into a paste and applied to zirconia restoration. The glaze layer with opal particles was fired according to the firing schedule of the glaze.

In examples 3 and 8, the heat-treated opal chunks were subjected to a double titania infiltration. The heat-treated opals chunks were infiltrated titanium isopropoxide for 2-10 hours and dried. In some embodiments, the chunks were allowed to sit in the isopropoxide for about 4 hours. The dried chunks were heated at 600° C. for 1 hour to yield titania infiltrated opal chunks. The titania infiltrated opal chunks went through titania infiltration process once more. In some embodiments, the infiltration step can be repeated 2 to 5 times. The double infiltrated chunks were ground into powder. The opal powder smaller than 63 μm was further milled in the ethanolic suspension into smaller particles. The particles were dried. Dried opal powder with titania double infiltration and glaze powder were mixed at a ratio of about 1:9 parts by weight. A range of about 1:1 to about 1:199 by weight may be employed. In some embodiments, the range is about 1:2 to about 1:99. In some embodiments, the range is about 1:3 to about 1:49. The mixed powder was made into a paste and applied to zirconia restoration. The glaze layer with opal particles was fired according to the firing schedule of the glaze.

In examples 4 and 8, the heat-treated opal chunks were subjected to a double titania infiltration and hydrolysis of titanium isopropoxide before post-heat treatment. The heat-treated opals chunks were infiltrated titanium isopropoxide for 2-10 hours and dried. In some embodiments, the chunks were allowed to sit in the isopropoxide for about 4 hours. The dried chunks were immersed in water to make the titanium isopropoxide hydrolyzed and heated at 600° C. for 1 hour to yield titania infiltrated opal chunks. Hydrolysis of titanium isopropoxide can prevent carbon residue generation after the heat treatment. The titania infiltrated opal chunks went through titania infiltration and hydrolysis processes once more. In some embodiments, the infiltration step can be repeated 2 to 5 times. The double infiltrated chunks were ground into powder. The opal powder smaller than 63 μm was further milled in the ethanolic suspension into smaller particles. The particles were dried. Dried opal powder with titania double infiltration and glaze powder were mixed at a ratio of about 1:9 parts by weight. A range of about 1:1 to about 1:199 by weight may be employed. In some embodiments, the range is about 1:2 to about 1:99. In some embodiments, the range is about 1:3 to about 1:49. The mixed powder was made into a paste and applied to zirconia restoration. The glaze layer with opal particles was fired according to the firing schedule of the glaze.

EXAMPLES

Example 1: 180 nm Ground Opal Powder with Dental Glaze Powder 7 g of silica spheres with about 180 nm size and 28 g of ethanol were added to each centrifuge tube to make 20 wt. % ethanolic suspension of silica spheres. The suspension was sonicated to break aggregates of the silica sphere. Centrifugation at low speed was done to remove large particles from the suspension. The supernatant suspension was decanted and transferred to another centrifuge tube. Sonication was applied again and centrifugation at high speed was done to form synthetic opals. Ethanol was decanted and the synthetic opal was dried at room temperature. The dried synthetic opal was heated at 600° C. for 4 h for consolidation of the opal. The heat-treated opals obtained from the general procedure were ground into powder. Opal powder smaller than 63 μm was further milled in the ethanolic suspension into smaller particles. The particles were dried. 5 g of opal powder and 45 g of glaze powder were mixed. The mixed powder was made into a paste and applied to a zirconia restoration. The glaze layer with opal particles was fired according to the firing schedule of the glaze.

Example 2: Titania Infiltration of the Synthetic Opal—180 nm 7 g of silica spheres with about 180 nm size and 28 g of ethanol were added to a centrifuge tube to make 20 wt. % ethanolic suspension of silica spheres. The suspension was sonicated to break aggregates of the silica sphere. Centrifugation at low speed was done to remove large particles from the suspension. The supernatant suspension was decanted and transferred to another centrifuge tube. Sonication was applied again and centrifugation at high speed was done to form synthetic opals. Ethanol was decanted and the synthetic opal was dried at room temperature. The dried synthetic opal was heated at 600° C. for 4 h for consolidation of the opal. The heat-treated opals chunks were infiltrated with titania by the following procedure. The chunks were immersed in titanium isopropoxide for 4 hours and dried. The dried chunks were heated at 600° C. for 1 h. The titania infiltrated chunks were ground into powder. Titania infiltrated opal powder smaller than 63 μm was further milled in the ethanolic suspension into smaller particles. The particles were dried. 5 g of opal powder with titania infiltration and 45 g of glaze powder were mixed. The mixed powder was made into a paste and applied to zirconia restoration. The glaze layer with opal particles was fired according to the firing schedule of the glaze.

Example 3: Double Titania Infiltration of the Synthetic Opal 7 g of silica spheres with about 180 nm size and 28 g of ethanol were added to a centrifuge tube to make 20 wt. % ethanolic suspension of silica spheres. The suspension was sonicated to break aggregates of the silica sphere. Centrifugation at low speed was done to remove large particles from the suspension. The supernatant suspension was decanted and transferred to another centrifuge tube. Sonication was applied again and centrifugation at high speed was done to form synthetic opals. Ethanol was decanted and the synthetic opal was dried at room temperature. The dried synthetic opal was heated at 600° C. for 4 h for consolidation of the opal. The heat-treated opals chunks were infiltrated with titania by the following procedure. The chunks were immersed in titanium isopropoxide for 4 hours and dried. The dried chunks were heated at 600° C. for 1 h. The titania infiltrated chunks went through titania infiltration process once more. The double infiltrated chunks were ground into powder. The opal powder smaller than 63 μm was further milled in the ethanolic suspension into smaller particles. The particles were dried. 5 g of the dried opal powder with titania double infiltration and 45 g of glaze powder were mixed. The mixed powder was made into a paste and applied to zirconia restoration. The glaze layer with opal particles was fired according to the firing schedule of the glaze.

Example 4: Double Titania Infiltration of the Synthetic Opal and Hydrolysis of Titania Precursor Before Post-Heat Treatment 7 g of silica spheres with about 180 nm size and 28 g of ethanol were added to a centrifuge tube to make 20 wt. % ethanolic suspension of silica spheres. The suspension was sonicated to break aggregates of the silica sphere. Centrifugation at low speed was done to remove large particles from the suspension. The supernatant suspension was decanted and transferred to another centrifuge tube. Sonication was applied again and centrifugation at high speed was done to form synthetic opals. Ethanol was decanted and the synthetic opal was dried at room temperature. The dried synthetic opal was heated at 600° C. for 4 h for consolidation of the opal. The heat-treated opals chunks were infiltrated with titania by the following procedure. The chunks were immersed in titanium isopropoxide for 4 hours and dried. The dried chunks were immersed in water for 4 hours to make titanium isopropoxide hydrolyzed and heated at 600° C. for 1 h. The titania infiltrated chunks went through titania infiltration and hydrolysis processes once more. The double infiltrated chunks were ground into powder. The opal powder smaller than 63 μm was further milled in the ethanolic suspension into smaller particles. The particles were dried. 5 g of the dried opal powder with titania double infiltration and 45 g of glaze powder were mixed. The mixed powder was made into a paste and applied to zirconia restoration. The glaze layer with opal particles was fired according to the firing schedule of the glaze.

Example 5: 220 Ground Opal Powder with Dental Glaze Powder 7 g of silica spheres with about 220 nm size and 28 g of ethanol were added to a centrifuge tube to make 20 wt. % ethanolic suspension of silica spheres. The suspension was sonicated to break aggregates of the silica sphere. Centrifugation at low speed was done to remove large particles from the suspension. The supernatant suspension was decanted and transferred to another centrifuge tube. Sonication was applied again and centrifugation at high speed was done to form synthetic opals. Ethanol was decanted and the synthetic opal was dried at room temperature. The dried synthetic opal was heated at 600° C. for 4 h for consolidation of the opal. The heat-treated opals were ground into powder. Opal powder smaller than 63 μm was further milled in the ethanolic suspension into smaller particles. The particles were dried. 5 g of opal powder and 45 g of glaze powder were mixed. The mixed powder was made into a paste and applied to zirconia restoration. The glaze layer with opal particles was fired according to the firing schedule of the glaze.

Example 6: Titania Infiltration of the Synthetic Opal—220 nm 7 g of silica spheres with about 220 nm size and 28 g of ethanol were added to a centrifuge tube to make 20 wt. % ethanolic suspension of silica spheres. The suspension was sonicated to break aggregates of the silica sphere. Centrifugation at low speed was done to remove large particles from the suspension. The supernatant suspension was decanted and transferred to another centrifuge tube. Sonication was applied again and centrifugation at high speed was done to form synthetic opals. Ethanol was decanted and the synthetic opal was dried at room temperature. The dried synthetic opal was heated at 600° C. for 4 h for consolidation of the opal. The heat-treated opals chunks were infiltrated with titania by the following procedure. The chunks were immersed in titanium isopropoxide for 4 hours and dried. The dried chunks were heated at 600° C. for 1 h. The titania infiltrated chunks were ground into powder. Titania infiltrated opal powder smaller than 63 μm was further milled in the ethanolic suspension into smaller particles. The particles were dried. 5 g of opal powder with titania infiltration and 45 g of glaze powder were mixed. The mixed powder was made into a paste and applied to zirconia restoration. The glaze layer with opal particles was fired according to the firing schedule of the glaze.

Example 7. Double Titania Infiltration of the Synthetic Opal—220 nm 7 g of silica spheres with about 220 nm size and 28 g of ethanol were added to a centrifuge tube to make 20 wt. % ethanolic suspension of silica spheres. The suspension was sonicated to break aggregates of the silica sphere. Centrifugation at low speed was done to remove large particles from the suspension. The supernatant suspension was decanted and transferred to another centrifuge tube. Sonication was applied again and centrifugation at high speed was done to form synthetic opals. Ethanol was decanted and the synthetic opal was dried at room temperature. The dried synthetic opal was heated at 600° C. for 4 h for consolidation of the opal. The heat-treated opals chunks were infiltrated with titania by the following procedure. The chunks were immersed in titanium isopropoxide for 4 hours and dried. The dried chunks were heated at 600° C. for 1 h. The titania infiltrated chunks went through titania infiltration process once more. The double infiltrated chunks were ground into powder. The opal powder smaller than 63 μm was further milled in the ethanolic suspension into smaller particles. The particles were dried. 5 g of the dried opal powder with titania double infiltration and 45 g of glaze powder were mixed. The mixed powder was made into a paste and applied to zirconia restoration. The glaze layer with opal particles was fired according to the firing schedule of the glaze.

Example 8: Double Titania Infiltration of the Synthetic Opal and Hydrolysis of Titania Precursor Before Post-Heat Treatment—220 nm 7 g of silica spheres with about 220 nm size and 28 g of ethanol were added to a centrifuge tube to make 20 wt. % ethanolic suspension of silica spheres. The suspension was sonicated to break aggregates of the silica sphere. Centrifugation at low speed was done to remove large particles from the suspension. The supernatant suspension was decanted and transferred to another centrifuge tube. Sonication was applied again and centrifugation at high speed was done to form synthetic opals. Ethanol was decanted and the synthetic opal was dried at room temperature. The dried synthetic opal was heated at 600° C. for 4 h for consolidation of the opal. The heat-treated opals chunks were infiltrated with titania by the following procedure. The chunks were immersed in titanium isopropoxide for 4 hours and dried. The dried chunks were immersed in water for 4 hours to make titanium isopropoxide and heated at 600° C. for 1 h. The titania infiltrated chunks went through titania infiltration and hydrolysis processes once more. The double infiltrated chunks were ground into powder. The opal powder smaller than 63 μm was further milled in the ethanolic suspension into smaller particles. The particles were dried. 5 g of the dried opal powder with titania double infiltration and 45 g of glaze powder were mixed. The mixed powder was made into a paste and applied to zirconia restoration. The glaze layer with opal particles was fired according to the firing schedule of the glaze.

The opals described above may be incorporated into a dental product to be applied to a restoration to achieve the desired aesthetics. Notably, these formulations can achieve the desired aesthetic in significantly less thickness than traditional materials.

Some embodiments provide a composition for imparting opalescence to a dental restoration, the composition comprising about 50-85% by weight of a ceramic component; about 0-2% by weight of a viscosity modifier; about 2-15% by weight of opal component; about 0-1% of a fluorescing agent; and the balance being a liquid component.

In some embodiments, the ceramic component is a ceramic base present at about 50-85% by weight.

In some embodiments, the opal component is present at about 2-6% by weight.

In some embodiments, the opal component is present at about 6-12% by weight.

In some embodiments, the ceramic component is a glaze base present at about 50-65% by weight.

In some embodiments, the opal component is present at about 6-15% by weight.

In some embodiments, such dental products are structure building compositions, comprising:
  about 50-85% by weight of a base ceramic;
  about 0-2% by weight of a viscosity modifier;
  about 2-12% by weight of opal;
  about 0-1% of a fluorescing agent;
  and the balance being a liquid component.

In some embodiments, such dental products are structure building compositions, comprising:
  about 50-85% by weight of a base ceramic;
  about 0-2% by weight of a viscosity modifier;
  about 2-6% by weight of opal;
  about 0-1% of a fluorescing agent;
  and the balance being a liquid component.

Other embodiments, are traditional glazes which do no substantially add structure, such dental products comprise:
  about 50-85% by weight of a glaze base;
  about 0-2% by weight of a viscosity modifier;
  about 6-16% by weight of opal;
  about 0-1% of a fluorescing agent;
  and the balance being a liquid component.

The base ceramic is an un-pigmented, un-opacified dental porcelain of an appropriate firing temperature for the system being used. This is consistent with the dental matrix described above.

The glaze base is an unpigmented, clear glazing porcelain of an appropriate firing temperature for the system being used. This is consistent with the glazes described above.

The viscosity modifier is any thickener suitable for use with the system being used. The viscosity modifier or modifiers can be optionally added to help control the consistency of the paste. The addition of a viscosity modifier aids in paste formation and can aid in imparting flow characteristics such as shear thinning, thixotropy, and/or shear thickening, if desired. The viscosity modifier can be selected from one or more of precipitated silica, fumed silica, polyethylene glycol, polyacrylic acid, salt of polyacrylic acid, polyvinyl alcohol, gums, saccharides, and organosilicones The Opal component refers to the synthetic opals described herein.

The liquid component provides a medium for the glaze base, and is driven off during the firing process. Suitable liquid components comprise at least one liquid selected from C1-C6 monoalcohols, C1-C6 diols, C1-C6 triols, tripropylene glycol, polyethylene glycol, polypropylene glycol, and water.

What is claimed is:

1. A composition for imparting opalescence to a dental restoration, the composition comprising about 50-85% by weight of a ceramic component, an opal component, and a liquid component, wherein the ceramic component is in the form of a dental glaze, a dental porcelain, or a dental ceramic.

2. The composition of claim 1, comprising:
   about 50-85% by weight of a ceramic component;
   about 1-20% by weight of opal component;
   and the balance being a liquid component.

3. The composition of claim 1, wherein the opal component is present at about 2-20% by weight.

4. The composition of claim 1, wherein the opal component is present at about 6-20% by weight.

5. The composition of claim 1, wherein the ceramic component is a glaze base present at about 50-65% by weight.

6. The composition of claim 1, wherein the opal component is present at about 6-15% by weight.

7. The composition of claim 1, further comprising less than about 2% by weight of a viscosity modifier.

8. The composition of claim 1, further comprising less than about 1% by weight of a fluorescing agent.

9. The composition of claim 1, further comprising:
   less than about 2% by weight of a viscosity modifier; and
   less than about 1% by weight of a fluorescing agent.

10. The composition of claim 1, wherein the opal component is colloidally assembled silica synthetic opal partially or fully infiltrated with ceramic.

11. The composition of claim 10, wherein the infiltrating ceramic contains one or more of titania, zirconia, alumina, yttria, zinc oxide, hafnia, tin oxide, indium oxide, ceria, niobium oxide, tantalum oxide, germanium oxide, gallium oxide, and scandium oxide.

* * * * *